United States Patent [19]
Patterson

[11] 4,291,980
[45] Sep. 29, 1981

[54] STYRENE-DIVINYLBENZENE COPOLYMER AND METHOD OF MANUFACTURE

[75] Inventor: James A. Patterson, Los Altos, Calif.

[73] Assignee: Amco Standards International, Mountain View, Calif.

[21] Appl. No.: 933,140

[22] Filed: Aug. 14, 1978

[51] Int. Cl.³ .............................................. G01J 1/02
[52] U.S. Cl. ................................................. 356/243
[58] Field of Search ....................................... 356/243

[56] References Cited
FOREIGN PATENT DOCUMENTS
1172061  7/1964  Fed. Rep. of Germany ...... 356/243

OTHER PUBLICATIONS

Patterson, "Preparation of Cross-Linked Polystyrenes and Their Derivatives for Use as Solid Supports or Insoluble Reagents", in *Biochemical Aspects of Reaction on Solid Supports*, Stark, ed. Academy Press, pp. 189–213, 1971.

*Primary Examiner*—Edward S. Bauer
*Assistant Examiner*—Matthew W. Koren
*Attorney, Agent, or Firm*—Limbach, Limbach & Sutton

[57] ABSTRACT

A unique styrene-divinylbenzene copolymer is taught together with its method of manufacture. The novel copolymer has been accepted as a definitive standard in the measurement of turbidity in water.

6 Claims, 4 Drawing Figures

U.S. Patent  Sep. 29, 1981  4,291,980
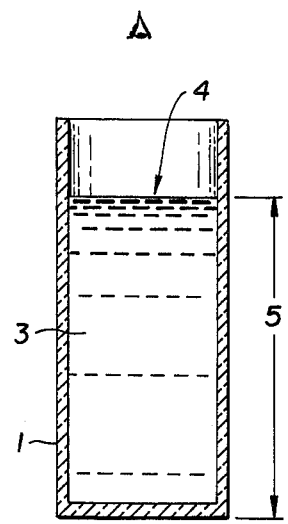
Fig._1.
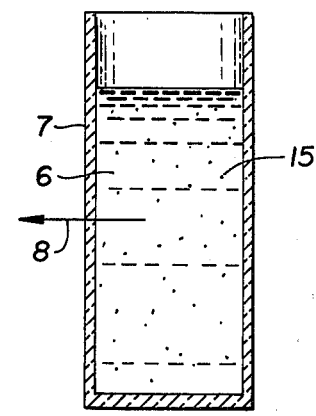
PRIOR ART
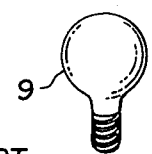
Fig._2.
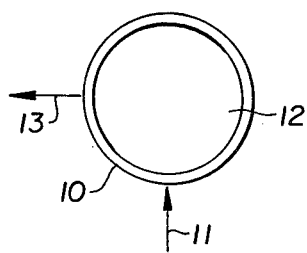
Fig._3B.
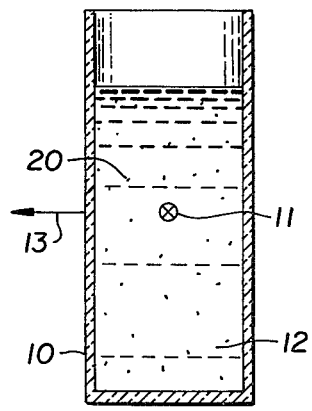
Fig._3A.

STYRENE-DIVINYLBENZENE COPOLYMER AND METHOD OF MANUFACTURE

BACKGROUND OF THE INVENTION

In testing and treating water for drinking purposes, it is necessary to test the water's turbidity. Turbidity has a marked effect on the bacteriological quality of water, whether or not disinfection is practiced. This is so because turbidity interferes with the ability to disinfect water. As recited in the Federal Register, Vol. 40, No. 248, published on Wednesday, Dec. 24, 1975, the maximum contaminant levels for turbidity were outlined as:

(a) one turbidity unit (NTU), as determined by a monthly average pursuant to section 141.22, except that five or fewer turbidity units may be allowed if the supplier of water can demonstrate to the state that the higher turbidity does not do any of the following:
(1) interfere with disinfections;
(2) prevent maintenance of an effective disinfectant agent throughout the distribution system; or
(3) interfere with microbiological determinations.
(b) Five turbidity units based on an average for two consecutive days pursuant to section 141.22.

Turbidity is measured by use of a turbidimeter which includes a light source for illuminating a sample to be tested and one or more photoelectric detectors with a readout to indicate the intensity of light scattered at right angles to the path of the incident light. The greater the scatter, the greater the turbidity. In testing for turbidity, a turbidity reference suspension must be selected which is readily reproducible and which can be used to calibrate the turbidimeter. Until the present invention, no such reference existed.

Prior attempts to measure turbidity were, in retrospect, rather crude. FIG. 1 shows the first accepted means of filling cylindrical container 1 with water 3 to a height 5. Candle 2 was placed at the bottom of the transparent cylindrical vessel. The illumination produced by the candle was viewed at the water surface 4. Simply stated, water level 5 was increased until the candle's illumination could no longer be seen at 4. The technique was proposed by Jackson and the height of the water was read in Jackson Turbidity Units (JTU). The result was a crude determination of the turbidity of water for as water became more turbid, the height 5 became smaller for a given sample.

The Jackson method can only be described as primative at best. The candle would blacken the bottom of the transparent vessel thus interfering with the pure turbidity measurement. Furthermore, sedimentation would precipitate out of solution and would block the candle's illumination, although such sedimentation has nothing to do with turbidity.

The next advance in turbidity measurement involved the use of formazin suspended in water as the reference. Formazin is the condensation polymer of hydrazine sulfate $(NH_2)_2H_2SO_4$ and hexamethylenetetramine $C_6H_{12}N_4$. Unfortunately, hydrazine compounds are extremely toxic and their use as a preparation of a turbidity standard for water represents certain disposal problems and health problems which should be avoided if possible. A further drawback to the use of formazin as a standard is that in the 1.0 and 5.0 NTU range, a non-linear dilution of formazin concentrate is necessary for, in such low concentrations, formazin decomposes. Formazin is prepared via a standard condensation reaction:

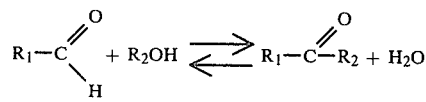

As the formazin solution becomes more dilute, the reaction is pushed to the left, thus breaking down the compound.

A further drawback experienced through the use of formazin is that it characteristically has a sedimentary light scatter loss of approximately 10% for four hours. This means that care must be given to thoroughly mix any formazin suspension prior to sampling. Such a problem can be more readily appreciated by viewing FIG. 2. The turbidity of a formazin containing standard is done by illuminating transparent cylinder 7 through its base by light source 9. The formazin 15 suspended in water 6 causes the light to scatter and a light reading is taken at right angles to the incidence of illumination at 8. The turbidity units are known as Formazin Turbidity Units (FTU). Again, the greater the turbidity, the greater the light scatter.

Because of the problems outlined herein, a formazin standard, although in use for over 40 years, is not at all accurate. The sedimentary light scatter loss is significant and, as was true with regard to the Jackson turbidity test, sediment acts to block the illumination source and results in false readings of the standard. Lastly, formazin diluted has a life expectancy of approximately one week while in a concentrated form its life expectancy is approximately 30 days.

It is thus an object of the present invention to eliminate the drawbacks as outlined above.

It is a further object of the present invention to provide a polymeric standard which can be used as a reference suspension for determining the turbidity of water without any of the drawbacks experienced when using formazin.

It is yet another object of the present invention to prepare a polymeric material which can be used as a standard reference suspension having a shelf life much longer than materials used for the identical purpose in the past.

It is yet another object of the present invention to prepare a polymeric material useful as a standard reference suspension in the measurement of turbidity in water which is non-toxic.

It is yet a further object of the present invention to produce a polymeric material useful as a standard reference suspension in measuring the turbidity of water which is stable at extremely low concentrations.

It is still another object of the present invention to produce a polymeric material useful as a standard reference suspension to measure turbidity in water which has a substantially lower loss in light scatter due to sedimentation than formazin and other prior art materials.

SUMMARY OF THE INVENTION

In measuring the turbidity of water, the method employed is based upon a comparison of the intensity of light scattered by the sample under defined conditions with the intensity of light scattered by a standard reference suspension. The higher the intensity of scattered light, the higher the turbidity. As expected, the measurements are only as accurate as the standard reference suspension allows. In order to prepare highly accurate standard reference suspensions, it was found that a polymer suspended in extremely turbidity-free water was needed wherein the polymer would exhibit virtually pure particle scatter with virtually no molecular light scatter. In order to accomplish this, a polymer was formulated wherein soluble molecular species within the polymeric lattice, both ionic and non-ionic could be easily removed.

It was also found that in order to provide a proper material for use as a standard in turbidity measurements, the particle would have to have an extremely long shelf life and be of a size which would approximate those impurities which normally cause water to be turbid such as spores and bacteriological growth. It was also found necessary to produce a particle which, when suspended in water, would remain suspended for an extremely long period of time so that the turbidity measurement can be taken without sedimentation. All of these necessary characteristics were achieved in producing the specific copolymer of styrene and divinylbenzene of the present invention.

The production of spherical beads comprised of copolymers styrene and divinylbenzene is well known. For example, see U.S. Pat. Nos. 2,366,007 and 3,463,320. However, until the present invention, no material such as a styrenedivinylbenzene copolymer could possibly act as an acceptable standard in turbidity measurement. More specifically, the particle should be spherical in nature and have a diameter approximately in the range of 0.2 microns to 1.0 microns. On a statistical basis, this means that approximately 90% of all beads produced should fall within the range. There are two basic types of polymerization systems; i.e., suspension and emulsion polymerizations. In suspension polymerization, which is classically an oil in water suspension wherein the oil phase is polymerized by the introduction of free radicals while the oil droplet suspension is maintained, the particles produced tend to have a diameter greater than 1.0 micron. If a classical emulsion polymerization is performed, wherein the polymer is built up from a solubilized phase of monomer, particles much smaller than 0.1 micron are produced. Thus, in order to arrive at an ideal particle size, the present invention has developed a unique polymerization process which is a cross between suspension and emulsion polymerization.

The key to the establishment of any reference or standard, particularly in the measurement of turbidity in water, is the reproducibility of the standard. In order to achieve reproducible results, it was necessary to produce a polymeric material which exhibits almost pure particle scatter. This means that the polymeric material would be extremely pure in nature and have very few impurities normally found in polymeric materials, such as unreacted monomers, trapped catalyst, stabilizing agents and other raw materials. The presence of such materials would cause the spherical particles to exhibit molecular light scatter which would vary from particle to particle, thus greatly reducing the effectiveness of the styrene-divinylbenzene particles as a true standard.

The spherical polymeric materials of the present invention have a specific gravity substantially that of water; i.e., between approximately 1.04 and 1.06. Thus, the present invention, when suspended in water, results in a random suspension which does not readily settle out and precipitate. As stated previously, prior art materials such as formazin precipitate at a rate of approximately 10% every four hours. Because of the ability to keep the particle of the present invention in random suspension for an extremely long period of time, a more accurate means of using the present invention as a standard has been developed.

BRIEF DESCRIPTION OF THE DRAWING

FIGS. 1 and 2 show prior art turbidimeters and
FIGS. 3A and 3B show turbidimeters according to the present invention.

DESCRIPTION OF THE PREFERRED EMBODIMENT

The use of the present invention as a standard in the measurement of the turbidity of water is shown in FIGS. 3A and 3B. Turning to FIG. 3A, particles 20 which represent the styrene-divinylbenzene copolymers of the present invention are suspended in extremely pure water 12. Light source 11 which is actually perpendicular to the plane of the drawing strikes substantially transparent cylindrical vessel 10. The suspended copolymers cause particle scatter which is read at right angles to the incident rays shown schematically at 13.

No longer does one have to illuminate the reference standard from the bottom of the cylindrical vessel and no longer does sedimentation yield false readings. In fact, the E.P.A. has adopted the present invention as the definitive means of testing the turbidity of water. Use of the present invention has been coined the Nephelometric Method and measurements made using it are reported in Nephelometric Turbidity Units (NTU). The product of the present invention is packaged in 1.0 NTU and 5.0 NTU concentrations although the turbidity values for given particle concentrations are quite reproducible over a wide range as follows:

| 90° Light Scatter vs Concentration | |
|---|---|
| NTU | p/ml (particles/milliliter) |
| 0.95 | $1.42 \times 10^8$ |
| 1.9 | $2.85 \times 10^8$ |
| 3.8 | $5.70 \times 10^8$ |
| 7.8 | $1.14 \times 10^9$ |
| 15.0 | $2.25 \times 10^9$ |
| 29.0 | $4.38 \times 10^9$ |
| 57.3 | $8.60 \times 10^9$ |
| 103.7 | $1.56 \times 10^{10}$ |
| 170.0 | $2.55 \times 10^{10}$ |
| 224.0 | $3.38 \times 10^{10}$ |

PREPARATION OF STYRENE-DIVINYLBENZENE COPOLYMERS

The copolymers of the present invention are prepared in a "support phase" which consists of ultrapure water; i.e., water which is at least 10 megohm or better, non-ionic, has no colloidal organic impurities and, finally, has a turbidity of 0.10 NTU or better. If water of such purity is not readily available, a centercut of distilled water can be filtered under a mixed bed deionization column and filtered under high pressure in an MSA packed filter bed.

Ideally, a media to monomer ratio should be approximately 10 to 1 by volume but can be as low as 5 to 1. Volumetric ratios which are higher than 10 to 1 tend to be so dilute that the polymerization becomes overly time-consuming and not cost-practical.

Monomeric styrene is marketed at extremely high purities (99% pure or better). However, divinylbenzene is traditionally no more than about 52% pure, for pure divinylbenzene tends to be extremely unstable. Some of the impurities found in divinylbenzene are various vinyl-substituted benzenes having the vinyl substitutions in the meta and ortho positions rather than the preferred para position and also products having saturated ethyl groups rather than the unsaturated vinyl groups. Divinylbenzene is also inhibited with approximately 150 ppm of tertiary butyl catachol (TBC). Styrene can also contain some TBC.

As an initial step, both the styrene and divinylbenzene monomers are purified with 6.0 N, sodium hydroxide in an extraction process to remove the TBC. The extraction process continues until, on a 10 to 1 monomer to hydroxide basis by volume, there is no color in the hydroxide layer in the separatory funnel.

After the hydroxide extract, the monomer is washed with distilled water three times in the funnel and dried over anhydrous calcium chloride.

Other impurities are removed from the divinylbenzene through the use of silica gel chromatographic purification. More specifically, a one-inch diameter by two-foot stopcock filtered glass column is packed to one-half its height with petroleum ether slurries of chromatographic grade silica gels. After the column is packed, nitrogen is passed therethrough to force out excess petroleum ether. The column is then loaded with the monomer to be purified. Although each monomer can be purified using the silica gel chromatographic purification technique, each monomer should be purified in its own column.

The packed column could handle about 10 times its volume of monomers. The flow rate of the monomer through the column should not exceed three-bed (silica gel) volume of monomer per hour. The first bed volume of monomers through the column will contain an excessive amount of petroleum ether and should be set aside for special handling or discarded. The remaining monomers which pass through the column are collected under nitrogen pressure in glass and sealed at approximately $-5°$ C. until used.

THE POLYMERIZATION REACTION

Surface active agents and surface stabilizing agents are employed in the polymerization process. It is important to select agents which are ionic in nature in order to aid in their removal after the polymerization process is complete. Representative of various surface active agents which are useful in practicing the present invention are purified sodium and potassium alkyl sulfates such as sodium 2-ethylhexyl sulfate and sodium heptadecyl sulfate, the most preferred being Tergitol 4T, a sodium alkyl sulfate anionic pure surface active agent produced by the Union Carbide Company. Proteins can be used as surface stabilizing agents. Examples of acceptable materials are any animal, vegetable or fish proteins which can be solubilized in water, although Knox gelatin powder was found to be perfectly acceptable.

The stabilizing agent is prepared by dissolving, for example, Knox gelatin powder in water to produce a 10% by weight viscous liquid. The liquid is heated to approximately 80° C. and filtered. The filtered protein solution can then be stored until needed.

A free-radical source is needed for the copolymerization reaction. A good free-radical source is benzoyl peroxide. Traditionally, when free-radical polymerization using benzoyl peroxide is carried out, a particle size of approximately 1 micron is achieved. However, it was found that when approximately 5 to 10 percent by weight benzoyl peroxide is used as the free-radical source, the number of free-radical sites for polymerization is increased which results in a decrease in the critical volume of the copolymer.

The polymerization is carried out by starting with a polymer kettle containing distilled water having dissolved therein approximately 1% by weight of the previously prepared surface stabilizing agent and approximately 0.1 percent by weight of the surface active agent. Nitrogen is used to flush the system for oxygen acts as a polymerization inhibitor. The mixer is started and the temperature of the solution raised to approximately 85° C. At this point, the monomers are added while rapidly stirring the media.

Characteristically, approximately 500 ml. of the monomer solution is added to a 4.0 liter polymer kettle at a total monomer to media ratio of 1 to 5, that is, a total media volume of 3.0 liters. The monomer mix generally comprises 20 percent by weight divinylbenzene, 5 percent to 10 percent by weight benzoyl peroxide, the remainder being styrene. The polymerization is continued under these conditions for approximately 30 minutes during which time microscopic samples of the mix are taken to insure that a proper bead size is being produced. If the mean size distribution of the suspended oil droplets is greater than desired, the size can be reduced by addition of more of the surface active agent. The estimation of size distribution of the oil droplets in suspension must be rapid, since any addition of the surface active agent must remain at least 10 minutes in the mixing solution to establish a new equilibrium in the new mean size.

Initially, an oil droplet size of less than 5 microns is tolerable. To achieve a final particle less than $1.0\mu$, surface active agent is added in an amount of approximately 0.5% by volume media-monomer per micron that the oil droplet is too large. In approximately 30 minutes time, the gel point is reached which causes the solution to increase in viscosity (the gel time being that time in which approximately 30 percent of the polymerization reaction has been carried out). The temperature is then increased to approximately 95° C. and the mix is refluxed for approximately 8 hours at this high temperature with mixing.

After the polymerization is approximately 95-99% complete, the solution is subject to steam distillation which maintains a temperature of approximately 100° C. During the steam distillation process, distilled water is added which results in a removal of any monomer which has not polymerized. The proteins which make up the surface stabilizing agent which remain in solution and on the surface of the polymeric beads are broken down during the steam distillation process into various amino acids.

The solution can then be allowed to cool to approximately 40° C. and is filtered through, for example, a 400 mesh stainless steel screen. The solution can then be passed through a 1 inch by 1 foot mixed bed deionized column at which time the pH of the solution is adjusted to approximately 2.2 through the addition of hydrochloric acid. The low pH further aids in ionization of the amino acids which resulted from a breakdown of the protein. The solution is then passed through a sodium cation column and re-passed through a mixed bed deionized column. In this way, all of the ionic materials such as unreacted stabilizing agents and surface active agents are collected resulting in a polymeric material which is capable of substantially pure light particle scatter.

The particles, once produced, are added to transparent cylindrical vessels which are sealed at specific concentrations to result in readings of 1.0 and 5.0 NTU. The suspensions remain stable for at least two years and can be used to calibrate turbidimeters as a necessary step in measuring the turbidity of water.

The Environmental Protection Agency has adopted the present invention as the definitive means of testing the turbidity of water. Section 141.22 of the Rules and Regulations of the Environmental Protection Agency's water programs as published in the Federal Register, Vol. 40, No. 248, of Wednesday, Dec. 24, 1975 states that "the measurement shall be made by the Nephelometric method . . . ." The Nephelometric method is the method of calibrating turbidimeters by using the copolymer suspension of the present invention. The present invention can perform its unique function because the polymeric material is spherical in nature comprising a substantially pure styrene-divinylbenzene copolymer wherein the spherical particle is substantially between 0.2 microns to 1.0 microns in diameter and exhibits substantially pure particle light scatter when suspended in a substantially turbidity-free media. The particle of the present invention is also characterized as having a specific gravity substantially between 1.04 and 1.06 which allows for maintenance of a copolymer suspension in pure water.

What is claimed is:

1. A suspension for measuring the turbidity of water comprising a suspension of substantially spherical particles in substantially turbidity-free water, said particles comprising substantially pure styrene-divinylbenzene copolymer wherein said spherical particles are substantially between 0.2 $\mu$m to 1.0 $\mu$m in diameter and which exhibit substantially pure particle light scatter when suspended is substantially turbidity-free water.

2. The suspension of claim 1 wherein the concentration of particles is such as to yield a turbidity reading of 1.0 NTU.

3. The suspension of claim 1 wherein the concentration of particles is such as to yield a turbidity reading of 5.0 NTU.

4. A method of determining the turbidity of water comprising:
  A. suspending substantially spherical particles in substantially turbidity-free water wherein said particles comprise substantially pure styrene-divinylbenzene copolymer having a particle size substantially between 0.2$\mu$ to 1.0$\mu$ in diameter and which exhibits substantially pure particle light scatter when suspended in a substantially turbidity-free media;
  B. placing said suspension in a substantially transparent cylindrical vessel;
  C. exposing the side wall of the vessel to a light source perpendicular thereto;
  D. reading the light which is scattered by said light source perpendicular to the incidence of said light source;
  E. performing steps C and D on a substantially transparent cylindrical vessel containing water of unknown turbidity; and
  F. comparing the amount of light scattered from said cylindrical vessel containing the suspended particles of the styrene-divinylbenzene copolymer with the amount of light scattered from said cylindrical vessel containing water of unknown turbidity.

5. The method of claim 4 wherein the particles of substantially pure styrene-divinylbenzene copolymer have a specific gravity substantially between 1.04 and 1.06.

6. The method of claim 4 wherein at least two suspensions of substantially pure styrene-divinylbenzene copolymer particles in substantially turbidity-free water are prepared to a concentration to yield turbidity readings of 1.0 NTU and 5.0 NTU.

* * * * *